United States Patent
Matsumura et al.

(10) Patent No.: US 10,755,427 B2
(45) Date of Patent: Aug. 25, 2020

(54) METHODS AND SYSTEMS FOR AUTOMATICALLY ANALYZING AN IMAGE REPRESENTATIVE OF A FORMATION

(71) Applicant: Schlumberger Technology Corporation, Sugar Land, TX (US)

(72) Inventors: Yuki Matsumura, Kyoto (JP); Tetsushi Yamada, Clamart (FR); Josselin Kherroubi, Clamart (FR); Isabelle Le Nir, Clamart (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 140 days.

(21) Appl. No.: 15/987,030

(22) Filed: May 23, 2018

(65) Prior Publication Data
US 2018/0342073 A1 Nov. 29, 2018

(30) Foreign Application Priority Data
May 23, 2017 (EP) ..................................... 17290068

(51) Int. Cl.
*G06K 9/00* (2006.01)
*G06T 7/529* (2017.01)
(Continued)

(52) U.S. Cl.
CPC ........... *G06T 7/529* (2017.01); *G01N 23/046* (2013.01); *G01N 33/24* (2013.01); *G01V 1/306* (2013.01);
(Continued)

(58) Field of Classification Search
CPC .......................................... G06T 2207/30181
See application file for complete search history.

(56) References Cited

U.S. PATENT DOCUMENTS

| 6,564,263 | B1 * | 5/2003 | Bergman | ................ | G06K 9/00 709/231 |
| 2013/0308831 | A1 * | 11/2013 | Dvorkin | ................ | E21B 47/00 382/109 |

(Continued)

FOREIGN PATENT DOCUMENTS

EP 3264335 A1 1/2018

OTHER PUBLICATIONS

Al-Sit. "Automatic Feature Detection and Interpretion in Borehole Data" Copyright (Year: 2015).*
(Continued)

*Primary Examiner* — Oneal R Mistry

(57) ABSTRACT

The disclosure relates to methods and systems for analyzing an image of the formation intersected by a borehole. One of the methods determines a local apparent dip of the borehole at least at a measured depth i represented on the image, applies at least a window to the image, wherein each of the windows includes one of the measured depth i and is shaped as a function of the determined local dip at the corresponding measured depth i, compares a texture of at least a first zone of each window and a texture of at least a second zone of said window, wherein each of the first and second zones are adjacent and shaped as a function of the determined dip. Based on the comparison, the method determines at least a location of a texture boundary and derives a property of the formation. The other method includes determine locations of the texture boundaries, segmenting the image as a function of the texture boundaries, and perform clustering of the segments in order to determine a facies of the formation.

20 Claims, 7 Drawing Sheets

(51) Int. Cl.
| | |
|---|---|
| G01V 8/02 | (2006.01) |
| G01V 3/38 | (2006.01) |
| G01V 5/12 | (2006.01) |
| G01N 23/046 | (2018.01) |
| G01N 33/24 | (2006.01) |
| G06T 7/40 | (2017.01) |
| G01V 1/50 | (2006.01) |
| G01V 1/30 | (2006.01) |
| G06K 9/46 | (2006.01) |
| G06K 9/62 | (2006.01) |
| G06T 7/12 | (2017.01) |
| G06T 7/42 | (2017.01) |
| G01V 3/18 | (2006.01) |
| G06T 7/143 | (2017.01) |

(52) U.S. Cl.
CPC ............... *G01V 1/50* (2013.01); *G01V 3/18* (2013.01); *G01V 3/38* (2013.01); *G01V 5/12* (2013.01); *G01V 8/02* (2013.01); *G06K 9/4642* (2013.01); *G06K 9/6219* (2013.01); *G06K 9/6223* (2013.01); *G06T 7/12* (2017.01); *G06T 7/143* (2017.01); *G06T 7/40* (2013.01); *G06T 7/42* (2017.01); *G01V 1/301* (2013.01); *G01V 2210/624* (2013.01); *G01V 2210/6244* (2013.01); *G01V 2210/74* (2013.01); *G06T 2207/10081* (2013.01); *G06T 2207/20076* (2013.01); *G06T 2207/30181* (2013.01)

(56) References Cited

U.S. PATENT DOCUMENTS

2013/0336541 A1* 12/2013 Spencer Elkington .. G06K 9/00
382/109

2014/0254884 A1* 9/2014 Elkington ............... G01V 1/42
382/109
2015/0009215 A1* 1/2015 Vallikkat Thachaparannbil .........
G06T 19/20
345/420

OTHER PUBLICATIONS

Stefan M. Luthi, "Textural Segmentation of Digital Rock Images into Bedding Units Using Texture Energy and Cluster Labels", Mathematical Geology. vol. 26. No. 2. 1994. (16 pages).

Margarete Linek, Matthias Jungmann, Thomas Berlage, Renate Pechnig and Christoph Clauser, "Rock classification based on resistivity patterns in electrical borehole wall images", J. Geophys. Eng. 4, pp. 171-183, 2007.

Matthias Jungmann, Margarete Kopal, Christoph Clauser and Thomas Berlage, "Multi-class supervised classification of electrical borehole wall image using texture features", Computers &Geosciences37, pp. 541-553, 2011.

Jana Zujovic, Thrasyvoulos N. Pappas, and David L. Neuhoff, "Structural Texture Similarity Metrics for Image Analysis and Retrieval", IEEE, 2013. (14 pages).

Stan Salvador, and Philip Chan, "Determining the Number of Clusters/Segments in Hierarchical Clustering/Segmentation Algorithms", IEEE, 2004. (9 pages).

Delhomme, J.P., 1992, "A quantitative characterization of formation heterogeneities based on borehole image analysis": Paper T presented at the SPWLA 33rd Annual Logging Symposium, Jun. 14-17, 1992. (25 pages).

Tuanfeng Zhang. Andriy Gelman, Robert Laronga, "Structure- and Texture-Based Fullbore Image Reconstruction", Mathematical Geoscience, 49, pp. 195-215, 2017.

J Portilla and E P Simoncelli A Parametric Texture Model based on Joint Statistics of Complex Wavelet Coefficients Int'l Journal of Computer Vision, 40(1), Oct. 2000, pp. 49-71.

* cited by examiner

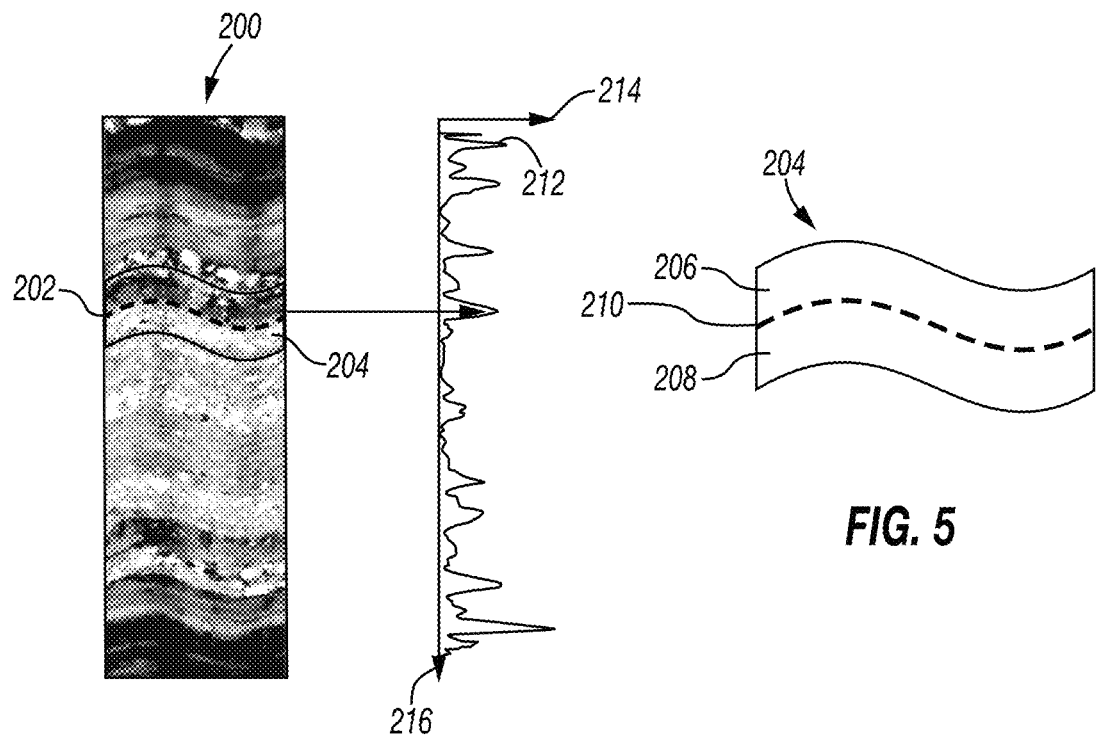
FIG. 4
FIG. 5
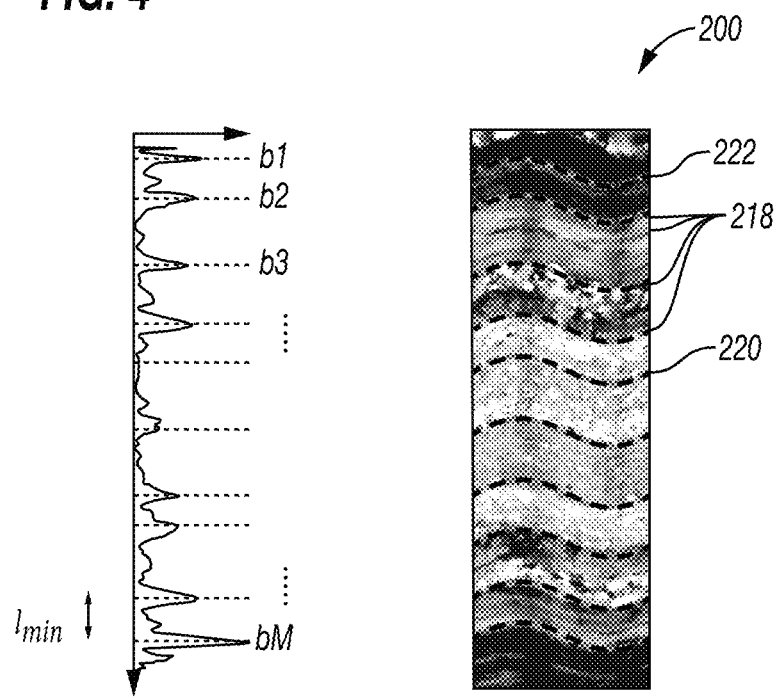
FIG. 7

METHODS AND SYSTEMS FOR AUTOMATICALLY ANALYZING AN IMAGE REPRESENTATIVE OF A FORMATION

BACKGROUND

The disclosure relates to methods and systems for analyzing an image of a geological formation, such as a borehole image.

One of the main tasks in geology is to describe and classify geological layers, in order to understand the subsurface structure and the geological history.

Reservoir evaluation in the oil industry aims at creating an accurate reservoir model. For this purpose, wells are drilled and the geological facies is evaluated. The term "facies" (or "lithofacies") denotes overall characteristics of such visual properties. The spatial analysis of facies in a geological field allows linking the distant layers, and identifying the geological structure.

Field geologists describe geological layers by observing rock samples by naked eye, or under microscope and classify the layers. They observe visual properties such as color, geometrical properties including grain size, because the origin of the rock and its history necessarily have an impact on its current visual properties (for example, color derives from mineral composition).

Conventionally, type of rock in the subsurface is also often characterized by electrofacies, which are properties obtained through geophysical logs such as resistivity and gamma ray. The definition of electrofacies deviates from the original definition of facies, because electrofacies does not necessarily differentiates "visible" rock properties. Electrofacies obtained from conventional logs is generally not as descriptive as facies in geology but it is linked to the facies (e.g. higher resistivity of rock is associated to larger grain size).

Borehole image is a type of log, which provides a high-resolution map of a specific property around borehole wall (for instance, the resistivity). Borehole images are often textured and accordingly provide both characteristics of electrofacies by the value of the property at each location, and the characteristics of facies by the textural properties. Borehole image, accordingly, is more descriptive to define rock properties than non-image type of logs.

In the present application, the term "texture" represents a pattern that is spatially homogeneous and consist of repeated elements, often subject to some randomization in their location, size, color, orientation, etc.

Currently, borehole images are analyzed by interpreters that are highly qualified geologists and are able to define facies based on the image texture. This task requires expertise and experience, and more importantly, it is time consuming.

SUMMARY

The current disclosure relates to a method for analyzing an image representative of a formation intersected by a borehole. The method includes determining a local apparent dip of the borehole at measured depths i represented on the image and applying windows to the image. Each of the windows includes one of the measured depth i and is shaped as a function of the determined local dip at the corresponding measured depth i, Each window includes a first and second zones adjacent and shaped as a function of the determined dip. The method also includes comparing a texture of the first and second zones, determine a location of texture boundaries on the image based on the comparison, and derive from the texture boundaries a property of the formation.

It also relates to a method for analyzing an image representative of a geological formation intersected by a borehole. The method includes determining a location of texture boundaries on the image and segmenting the image in several segments based on the determined texture boundaries. A plurality of segments are indeed each delineated by adjacent texture boundaries. The method also includes clustering segments into groups based on texture features representative of each segment. During the clustering, two different segments may be assigned to an identical group. The method also includes determining a facies of a formation based on the clustering.

The disclosure therefore aims at defining operations that will enable to automatically or semi-automatically determine texture boundaries existing between different layers of the geological formation based on the texture features of the borehole image, allowing to derive at least a formation property. The methods according to the disclosure may for instance facilitate the determination of bed boundaries and/ or the facies of the geological formation, following the texture boundaries determination, therefore at least significantly diminishing the analysis time.

Further, the methods defined hereinabove determine the facies of the geological formation using a limited number of computations, enabling an analysis of complex images with a reasonable computing power.

The disclosure also related to systems for analyzing an image representative of a formation intersected by a borehole. Each of the systems includes a set of processors comprising at least a processor and configured for performing one of the methods disclosed hereinabove.

BRIEF DESCRIPTION OF THE DRAWINGS

Various aspects of this disclosure may be better understood upon reading the following detailed description and upon reference to the drawings in which:

FIG. 4 shows a borehole image and an output of an operation of the method, namely an operation of calculating a boundary likelihood, according to an embodiment of the disclosure, FIG. 5 shows a window used for performing the calculation on the borehole image of FIG. 4, FIG. 7 shows an output of a later operation of the method according to an embodiment of the disclosure, i.e. determining a location of a texture boundary on the borehole image of FIG. 4.

DETAILED DESCRIPTION

Figure 1:
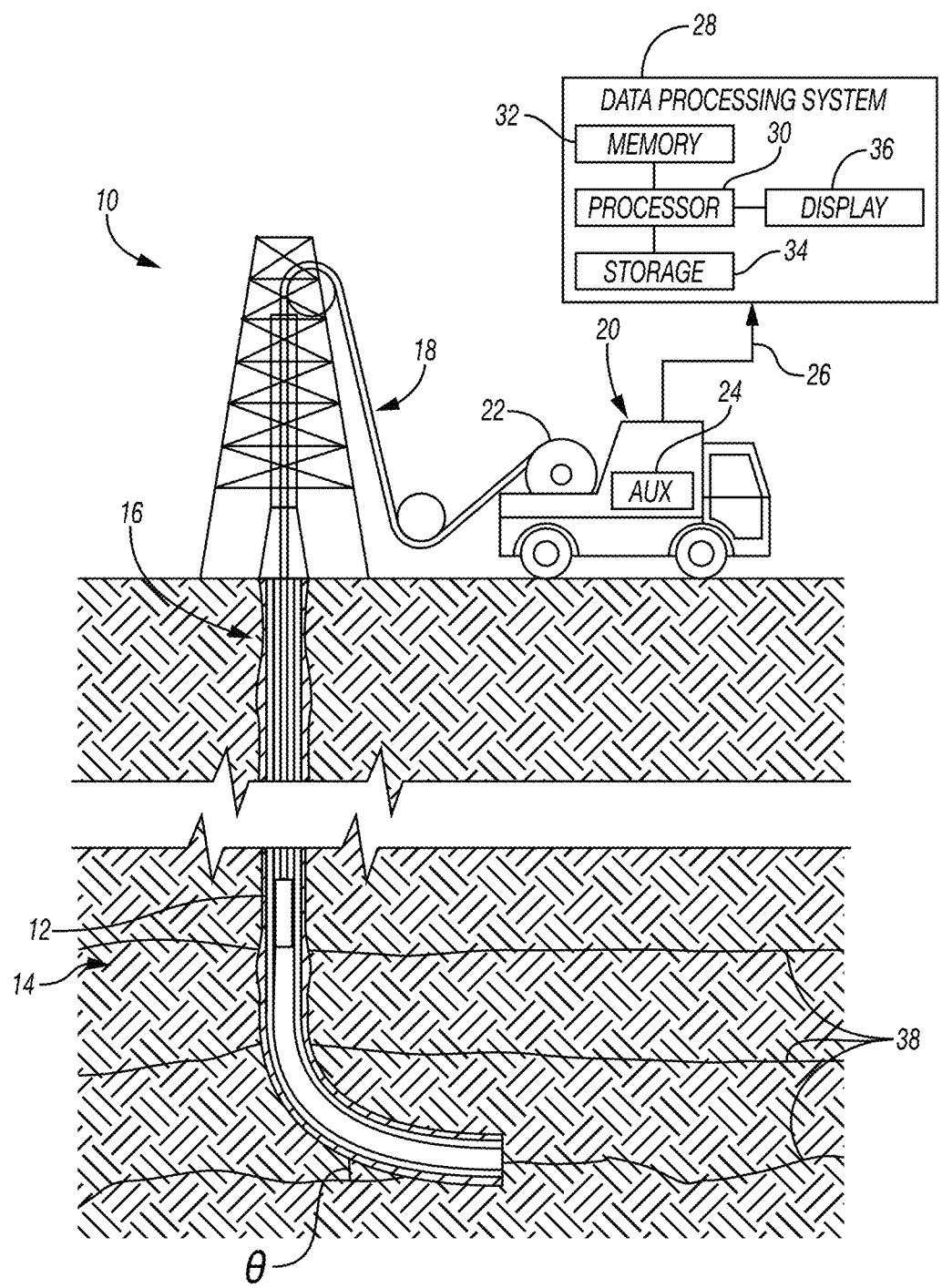
FIG. 1 is a schematic diagram of a well-logging system that acquires images of a borehole, in accordance with an embodiment of the disclosure.

One or more specific embodiments of the present disclosure will be described below. These described embodiments are examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.'

The disclosure discloses a novel method for analyzing images representative of a geological formation. In the following specification, an image may be a photograph of a portion of the formation, such as a borehole wall or a core, or a type of log, which provides a high-resolution map of a specific property of the portion of the formation. Such images may be obtained downhole by measuring acoustical properties of the borehole, nuclear properties of the borehole (such as spectral gamma ray) or electromagnetic properties of the borehole (such as resistivity). They may also be obtained at the surface by submitting of rock cores to a CT Scan. In the present specification, the method is described in relationship to an electromagnetic image but the method is applicable to any image representative of the geological formation. The image representative of the formation may be designated in the following as "borehole image", "image of the borehole", "image of the borehole wall" or simply "image".

When a well is drilled through a geological formation, the well may pass through numerous layers of different types of rock. Each of these may be referred to as a formation bed, and the interface between different beds may be referred to as a bed boundary. The bed boundaries form part of the structure of the geological formation. Knowing the placement of the bed boundaries in the geological formation thus may help define the facies on the borehole wall and locate zones of interest, such as those that contain oil, gas, and/or water.

Many downhole tools used for logging new wells obtain measurements of the formation supporting the wells. As mentioned above, a well-logging system may be used to obtain an image of borehole wall that may correspond to a well used to produce hydrocarbons from geological formations within the Earth. Moreover, the well-logging system may analyze the image of the borehole to identify bed boundaries and/or facies of the geological formation intersected by the borehole.

With this in mind, FIG. 1 is a schematic diagram illustrating a well-logging system 10 that may obtain borehole images at variable depths of a formation, in accordance with an embodiment. The well-logging system 10 may be conveyed through a geological formation 14 via a borehole 16. A downhole tool 12 may be conveyed on a cable 18 via a logging winch system 20. Although the logging winch system 20 is schematically shown in FIG. 1 as a mobile logging winch system carried by a truck, the logging winch system 20 may be substantially fixed (e.g., a long-term installation that is substantially permanent or modular). Any suitable cable 18 for well logging may be used. The cable 18 may be spooled and unspooled on a drum 22 and an auxiliary power source 24 may provide energy to the logging winch system 20 and/or the downhole tool 12.

Although the downhole tool 12 is described as a wireline downhole tool, it should be appreciated that any suitable conveyance may be used. For example, the downhole tool 12 may instead be conveyed as a logging-while-drilling (LWD) tool as part of a bottom hole assembly (BHA) of a drill string, conveyed on a slickline or via coiled tubing, and so forth. For the purposes of this disclosure, the downhole tool 12 may be any suitable measurement tool that obtains multidimensional measurements through depths of the borehole 16.

Many types of downhole tools may obtain measurements in the borehole 16. For each depth of the borehole 16 that is measured, the downhole tool 12 may generate log data (e.g., an image of a measured property that is representative of the borehole). The downhole tool 12 may provide such measurements 26 to a data processing system 28 via any suitable telemetry (e.g., via electrical signals pulsed through the geological formation 14 or via mud pulse telemetry, generally in the case of LWD tool). The image of the borehole wall is representative of the formation and may be obtained by measuring acoustical properties of the borehole, optical properties of the borehole (via a camera for instance), nuclear properties of the borehole (such as spectral gamma ray) or electromagnetic properties of the borehole (such as resistivity). The downhole tool may be configured to measure the property of interest in a formation intersected by a borehole that was drilled using water based mud or oil based mud (for resistivity in particular, the downhole may be specifically configured taking into account the type of mud). Generally, the image may originate from any appropriate tool. It will also be noted that the method that will be disclosed below is also applicable to other type of images, for instance images obtained from rock cores analysis.

The data processing system 28 may process the measurements 26 to identify patterns related to properties of the geological formation 14. The patterns in the measurements 26 may indicate certain elements of the formation 14 at the intersection with the borehole 16 such as bed boundaries or facies that could be otherwise not be observed by a human operator or identified after a significant time of analysis.

To this end, the data processing system 28 thus may be any electronic data processing system that may be used to carry out the methods of this disclosure. This data processing system 28 is shown at the rig site on FIG. 1 but it could be situated at least partially away from the rig site, for instance connected to the rig site via a network. In another embodiment, it could also be located partially or totally inside of the downhole tool.

The data processing system 28 may include a processor 30, which may execute instructions stored in memory 32 and/or storage 34. As such, the memory 32 and/or the storage 34 of the data processing system 28 may be any suitable article of manufacture that can store the instructions. The memory 32 and/or the storage 34 may be ROM memory, random-access memory (RAM), flash memory, an optical storage medium, or a hard disk drive, to name a few examples. A display 36, which may be any suitable electronic display, may provide a visualization, a well log, or other indication of properties of the formation 14 based on the measurements 26.

As will be discussed in more detail below, the data processing system 28 (or processing circuitry of the downhole tool 12) may use the measurements 26 (e.g., borehole image data) to determine properties of the formation 14, such as bed boundaries or facies at the intersection with the borehole.

As shown in FIG. 1, the borehole 16 may be at least partially horizontal and drilled through a plurality of beds of the formation 14. Boundaries 38 represents the planar interface between these different layers of the formation 14. The borehole 16 intersects the formation boundary 38 at a relative angle θ, which also represents the dip (i.e. the plane in which the formation features cross the borehole). As can be seen on FIG. 1, the angle θ may vary in function of the well deviation and/or inclination of the boundaries.

Figure 2:
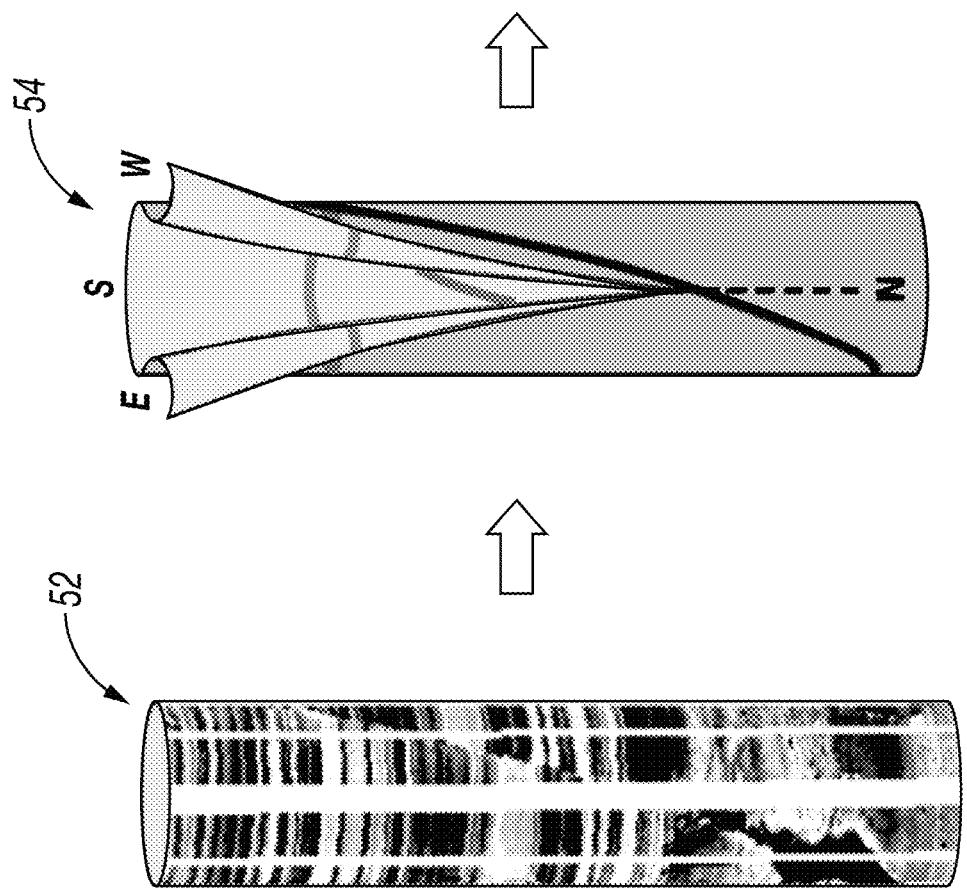
FIG. 2 is an example image of a borehole acquired by the well-logging system of FIG. 1, in accordance with an embodiment of the disclosure.
Figure 2:
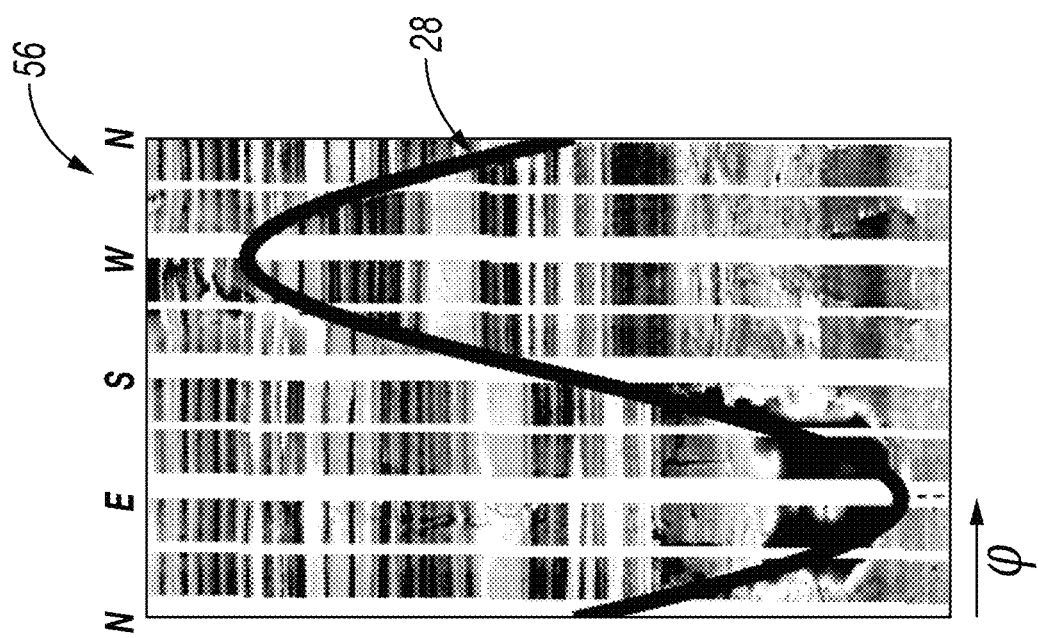

With the foregoing in mind, the borehole image data acquired via the downhole tool 12 may include high-resolution measurements that enable the data processing system 28 to characterize properties of the formation, such as location of the bed boundaries or facies at the intersection with the borehole. In one embodiment, as shown in FIG. 2, the downhole tool 12 may acquire imaging measurements (e.g., borehole image data) on a cylinder-shaped borehole by scanning 360° around the borehole 16. After receiving the cylinder-borehole image data 52, the data processing system 28 may convert the cylinder-shaped image (e.g., 54) into a unrolled image 56 and acquire certain imaging measurements as a result of unrolling the cylinder-shaped image. As such, the apparent azimuth angle reads on the horizontal axis of the unrolled image 56 and the vertical axis represents the measured depth. By inspecting the unrolled image 56, the downhole tool 12 may enable someone to identify any planar event crossing the borehole 16 based on a one period sinusoid 58 depicted on the unrolled image 56. In one embodiment, the data processing system 28 may analyze the unrolled image 56 and extract properties of the formation from the image. The "borehole image" analyzed in the method described in the following is an unrolled image.

Figure 3A:
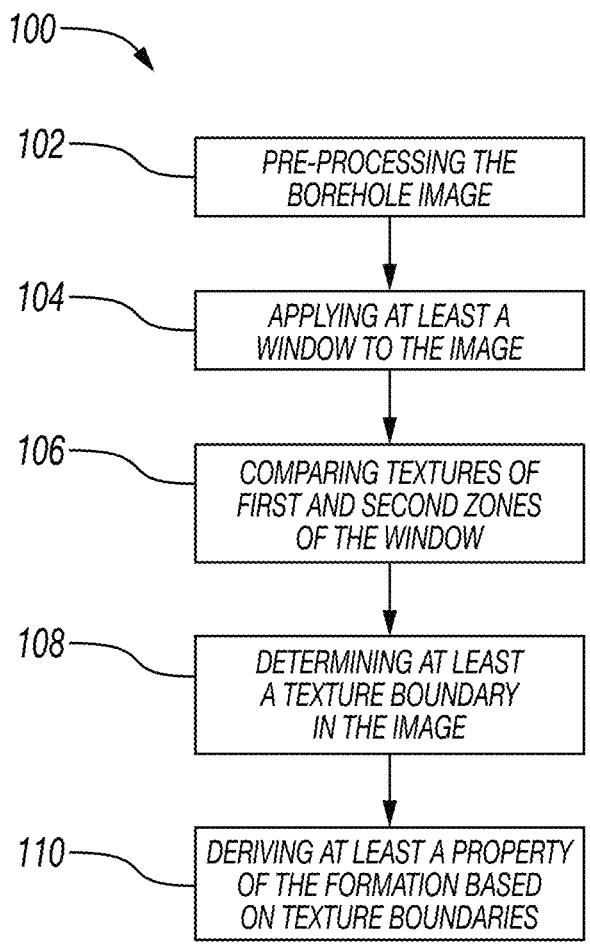
FIG. 3A is a flow diagram of a method for analyzing a borehole image according to an embodiment of the disclosure.
Figure 3B:
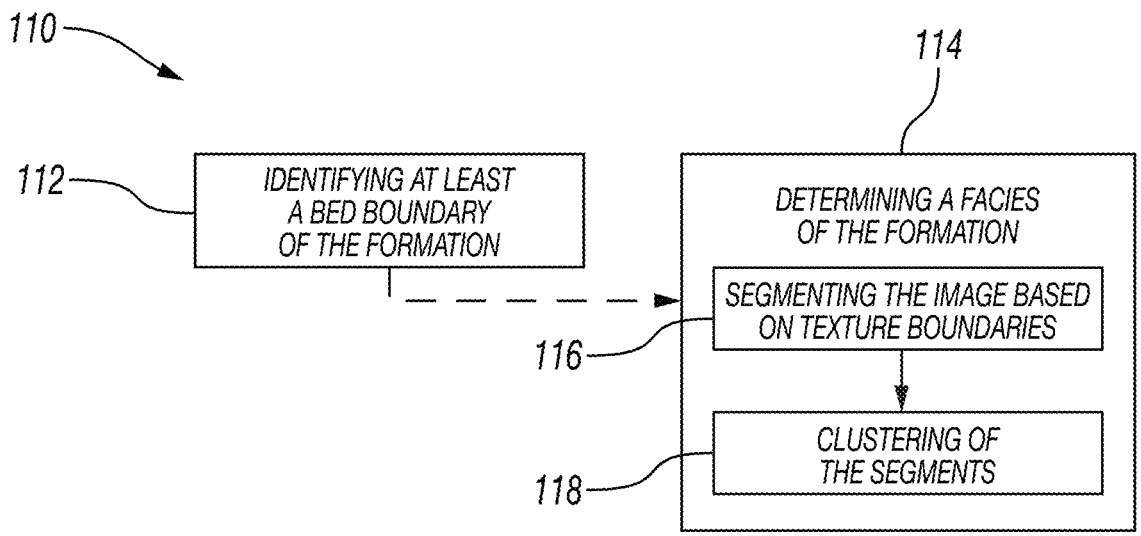
FIG. 3B is a flow diagram of an operation of method of FIG. 3A.

As shown on FIG. 3, the method 100 according to an embodiment of the disclosure first comprises pre-processing the image obtained via a downhole tool (block 102). The pre-processing operations may comprise standard pre-processing generally applied to borehole images, such as depth correction, image harmonization, and calibration in order to obtain an interpretable borehole image. Other pre-processing techniques may include filling in the missing values between pads (in case of wireline tools) using geostatistical methods as per well-known methods. Such missing values are visible on the image of FIG. 2. Further pre-processing technique may include equalizing the image values over the whole interval.

The pre-processing operation also includes at least determining a local apparent dip of the borehole. The apparent dip may be determined by analyzing the borehole image, manually or automatically by any well-known process. The local dip is the local value of the dip at a predetermined measured depth. Indeed, as the dip varies as a function of several parameters related to borehole and formation, the dip appears also to vary on the borehole image with regard to measured depth. A method for determining the local dip is for instance disclosed in patent application EP 16290116.9, but any known method is appropriate. The dip may also be determined independently from the image, for instance via accelerometer measurement performed downhole.

Figure 6A:
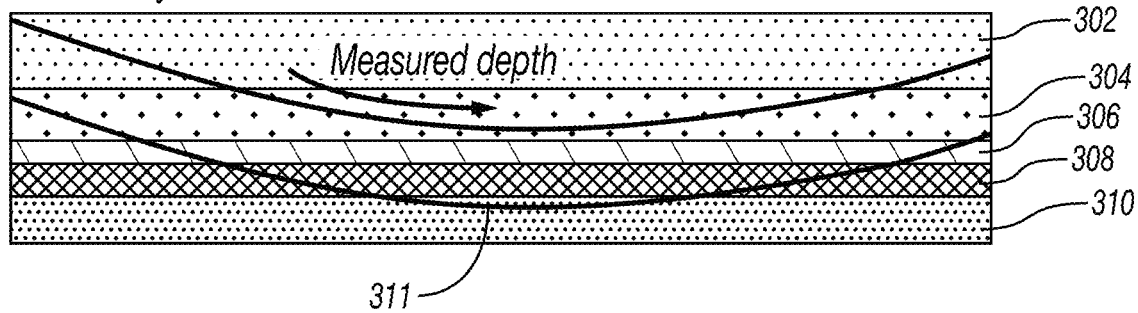
FIG. 6A is a portion of a trajectory of a borehole in a geological formation and FIG. 6B is the corresponding image of the formation

As seen on the pre-processed image 200 of FIG. 4, a dip may appear as a sinusoid 202, typically on vertical wells, wherein the features of the sinusoid and in particular its amplitude depends on the angle θ at which the borehole intersects the formation boundaries. A dip may also appear as bull-eye or reverse bull eye, typically in horizontal wells as shown in more details on FIGS. 6A and B. Indeed, when drilling almost horizontally and encountering bed boundaries the upper part of the borehole 311 may remain in upper layers 302, 304 while the bottom part of the borehole crosses lower layers 306-310. The image of the formation intersected by the borehole in function of the measured depth then shows the layers appearing as circular patterns called bull's eye. In this case, the dip is not a sinusoid but an elliptical shape as evidences by the visible boundaries such as boundary 312.

Figure 6B:
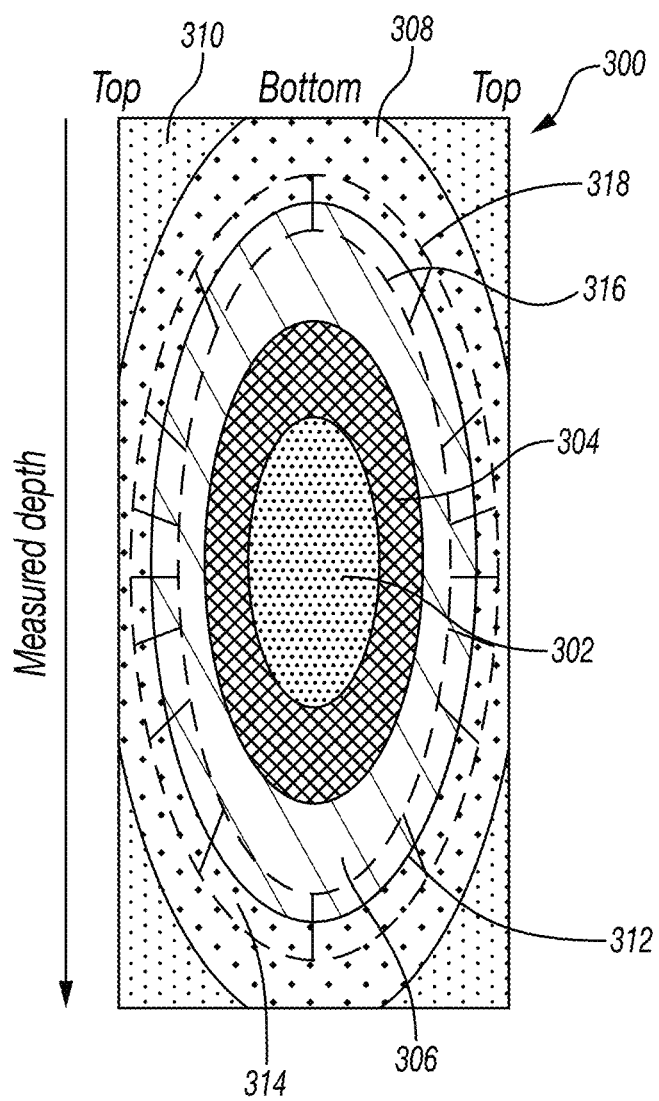

The method also includes applying (block 104) one or several windows (shown as 204 on FIGS. 4 and 314 on FIG. 6B) as defined on the image 200. Each window is defined to follow the local dip, appearing for instance as a sinusoid 202 in image 200. Therefore, a window that is applied at a predetermined measured depth i has a shape depending on the local dip at measured depth i. The depth i may for instance be defined as being the center of the window along a direction perpendicular to the dip (in the vertical direction here).

The window may be defined so that its dimension in the direction perpendicular to the dip average direction (i.e. the vertical direction in the image 200) is not bigger that twice a minimal thickness $l_{min}$ of a layer in a geological formation. It simplifies the analysis as only two layers may be represented in each of the windows, and allows to obtain more consistent results. The vertical dimension of the window (and minimal thickness as shown on the image) may be determined as a function of the dip. In an alternative embodiment, the dimension of the window may be preset, not taking into account the dip.

In the case of a vertical well having a sinusoidal dip, the window 204 is a vertical window delineated by an upper and a lower sinusoid, as shown on FIG. 4. In the case of a horizontal well (as shown on FIGS. 6A & B), the window 314 may be a closed ring-like shape following the bull's eye dip line (corresponding to boundary 312 as the boundary is horizontal) at its external and internal borders 316, 318 and centered on the same point as the dip line—i.e. parallel to the dip line. The minimal thickness defines the distance between the external and internal borders of the window. Contrary to the vertical configuration, in which several windows defined by the same local dip and the same minimal thickness $l_{min}$ are of exactly identical shape, in the horizontal configuration, the ring-like shapes forming the windows have the same center and distance between internal and external borders but may have different external borders and are therefore not of exactly identical shape.

In an embodiment, a sliding window is applied to the image so that any pixel of the image is contained in at least a window. The successive windows are sampled at a sampling distance along the direction perpendicular to the dip (vertical direction in section 200) which is at minimum the dimension of a pixel but may be the dimension of a plurality of pixels depending on the expected resolution and/or expected computation time. When the well is a vertical well, the window slides in the vertical direction of the image and when the well is a horizontal well, the window slides along the radius of the ring-like shape forming the window. However, this is a particular embodiment of the method. In another embodiment, the method may only apply a unique window to the image, and analyze the image only inside of the window to determine formation properties inside of the window.

The method also includes comparing (block 106) a texture of a first zone of the window and a second zone of the window 204 adjacent to each other, the first and second zone being separated by an intersection line also defined to follow the dip. In an embodiment described in more details below the first 206 and second 208 zones are the top half and the bottom half of the window and the intersection line 210 separates the window in two exactly equal zones. The intersection line 210 is also parallel to the sinusoid 202 and therefore to upper and lower borders of the window. When the dip appears as a bull's eye, the intersection line follows the internal and external borders of the ring-like shape. In an embodiment of the disclosure, only one comparison is performed per window, as shown on FIG. 5. Of course, the intersection is arbitrarily chosen so that the first zone corresponds to the upper half and the second zone to the lower half but any other distribution between first and second zones may be chosen as long as the intersection line follows the dip. The dip generally does not vary significantly locally. However, for a higher accuracy, it is recommended that the depth i of the intersection line is the depth i of the local dip used for defining the window.

Comparing the texture of the first and second zone includes calculating a boundary likelihood for each window. In an exemplary embodiment, the set of points of the top half of the window is designated $w_i^{Top}$ and the set of points of the bottom half is designated $w_i^{Bottom}$ when the separation line between the top and bottom half is situated at location i (corresponding to measured depth i when the well is vertical).

The dissimilarity between the texture of the sets $w_i^{Bottom}$ and $w_i^{Bottom}$ corresponds to the boundary likelihood. Indeed, when the image does not show the same features on the top and bottom halves on the window, it is likely that the layers represented in the corresponding halves are not the same The likelihood is calculated by:

$$L_i = \text{Dissimilarity}(w_i^{Top}, w_i^{Bottom}).$$

The dissimilarity analysis is based on texture features of each of the upper and lower zones 206, 208, for instance luminance or color components. Any metrics may be used for the dissimilarity function. In one embodiment, the variations of Structural Texture Similarity (STSIM) defined based on the texture features of a luminance component, such as luminance term (mean of luminance component, contrast term (standard deviation of luminance component) and cross-correlation coefficient. The STSIM is described in more details in the publication from Jana Zujovic, Thrasyvoulos N. Pappas, and David L. Neuhoff, named "Structural Texture Similarity Metrics for Image Analysis and Retrieval", (IEEE2013). It ranges from zero (dissimilar) to one (identical). The dissimilarity function may then be defined as:

$$\text{Dissimilarity}_i = 1\text{STSIM}(w_i^{Top}, w_i^{Bottom}).$$

An alternative calculation of boundary likelihood may include calculating the distance between N-dimension feature vectors extracted from each images that may have been previously submitted to filtering, for example, using an appropriate Gabor filter F. These vectors may relate to statistical variables (mean, variance, etc.) relative to texture features on the (filtered) entire zone. Such a distance may be a Euclidian distance or a Mahalanobis distance. The dissimilarity at location i may be expressed as follows:

$$\text{Dissimilarity}_i = \text{Distance}(F(w_i^{Top}), F(w_i^{Bottom}))$$

This comparison may be performed for each of the windows and associated to the location at which the intersection line between first and second zone is set.

In another embodiment, different intersection lines (all following the dip) may define several first and second zones within the same window and the dissimilarity between each first and second zone may be calculated and associated with the location of the intersection line.

The method may then include determining a least a location of a texture boundary inside of the image (block 108), in particular in one of the windows This may include optionally plotting the boundary likelihood versus the location i for each section. A curve 212 obtained by applying the above-mentioned dissimilarity indicator based on STSIM comparison to the image 200 is shown on FIG. 4. The curve represents dissimilarity (214, on horizontal axis) versus measured depth (216, on horizontal axis). Determination of texture boundaries may also include identifying a set of locations $b_m$ that satisfy conditions that are likely to indicate the presence of texture boundaries. A first condition may be that the likelihood value of the location $b_m$ corresponds to the local maxima of the curve. A second condition may be that the likelihood value of the location $b_m$ is in a certain range.

Another condition that may be used to select the boundaries, is to select the locations $b_m$ that satisfy the following set of equations:

$$\underset{b_1, b_2, \ldots, b_M}{\text{maximize}} \sum_{m=1}^{M} L_{b_m}$$

$$\forall m \in \{1, \ldots, M1\}, b_{m+1} b_m > l_{min},$$

Wherein $L_{b_m}$ is the likelihood value associated to the location $b_m$, M any integer for which the above-mentioned equations are satisfied and $l_{min}$ the minimal thickness of a geological layer as defined above. This constrained maximization enables to choose boundaries with higher boundary likelihood, keeping the distance more than minimal possible distance $l_{min}$ between adjacent boundaries.

The conditions that are determined above may be cumulative or alternative. The output of one of the conditions may be applied as an input to another condition. For instance, FIG. 7 shows, on the curve 212 and on the corresponding image 200, the boundaries $b_m$ that have been determined from the image with a determination process comprising first, determining the local maxima and second, solve the set of equations of the third condition with only local maxima as inputs $b_m$ for the set of equations. Such combination gives an accurate output relative to the location of the texture boundaries, while the time of the computation remains reasonable.

The method according to the disclosure may then comprise deriving a property of the formation based on the location of texture boundaries (block 110). This operation is shown in more details on FIG. 3A.

In one embodiment, deriving a property of the formation includes identifying the location of bed boundaries (block 112). Indeed, the location of texture boundaries generally correspond to location of bed boundaries forming the interface between two layers of the formation.

The image 200 including the texture boundaries 218, 220, 222 of FIG. 7 enables to notice that the results of the boundary determination are satisfying. All the texture boundaries are representative of bed boundaries except for boundary 220 and boundary 222.

Of course, the determined location of bed boundaries may be validated or corrected by an expert once the texture boundaries have been computed following the above-mentioned operations. Some texture boundaries may indeed not correspond to bed boundaries (for instance, because they correspond to other events of the borehole such as fractures). Other bed boundaries may not correspond to a change of the texture in the image and are not detected only with operations shown above. However, the above-mentioned method facilitates the boundary detection by identifying a significant set of the boundaries.

Figure 8:
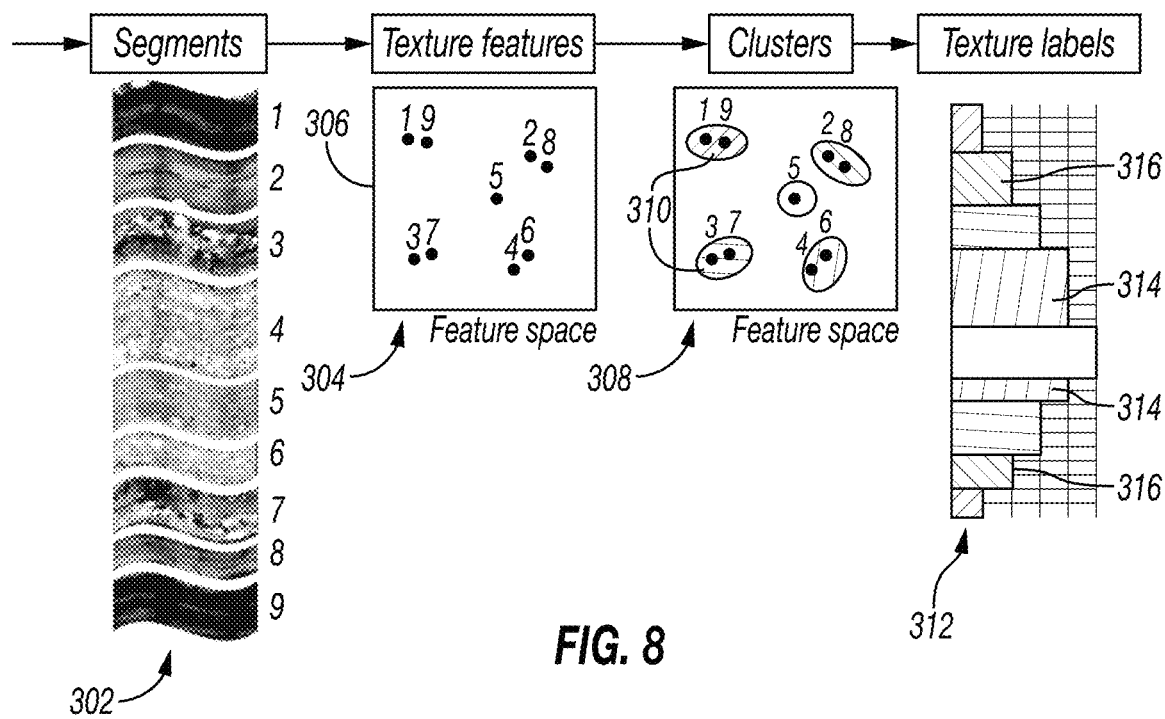
FIG. 8 is a flowchart showing details and output of further operations of the method according to an embodiment of the disclosure, on the borehole image of FIG. 4, i.e. segmenting the image and clustering the segments.

Deriving at least a property of the formation may also include determining a facies of the formation intersecting the borehole (block 114). In this case, the method may also include segmenting the image in several segments based on the determined texture or bed boundaries (block 116). Each segment is delineated by adjacent boundaries (segments 1 to 9 of operation 302 in FIG. 8). On FIG. 8, the boundaries used for the facies determination are bed boundaries (texture boundaries 220, 222 not corresponding to bed boundaries have been removed). However, the facies determination 114 may be performed without determining the bed boundaries and derived directly from the texture boundaries.

Once the segments of the image have been defined, clustering is implemented with entire segments as an input (block 118). Contrary to an ordinary clustering method, the image is not clustered by analyzing each pixel. The clustering includes grouping the segments with similar texture features.

The clustering may be performed by using an indicator representative of the texture features of each segment. The texture features may be based on statistical variables (such as mean and variance) taking into account one or several texture properties of all of the pixels belonging to the segment, optionally once the image has been filtered. Operation 304 shows a map 306 of texture indicators associated with each of the segments 1 to 9. The dissimilarity between two different segments may then be determined. The dissimilarity may be computed for all pairs of segments. Dissimilarity between indicators may be computed as defined earlier in the specification. Any other appropriate dissimilarity function may also be used. Based on the dissimilarity between segments, clusters 310 are formed as shown associated with operation 308 of FIG. 8. For forming these clusters, any type of clustering method may be used, such as statistical clustering based on Gaussian mixture model and K-means. Among different methods, agglomerative hierarchical clustering may be used.

Once clustering has been performed, group identifiers 314, 316 are assigned to each of the segments as shown on operation 312 wherein group identifiers are plotted versus measured depth. Group identifiers identify at least segments belonging to the same cluster as rocks of the same nature that have texture features of the same type on the image. Segments 4 and 6 are assigned the same group 314 while segments 2 and 8 are assigned another group 316.

The method may include additional optional post-processing (not represented) including automatically removing inappropriate texture boundaries not corresponding to bed boundaries (if not done at the end of the operation 110) by identifying adjacent segments assigned to a same group. Such post-processing (coupled for instance with a threshold on a dissimilarity value) at the inappropriate texture boundary location may also enable automatic identification of other zone of interest of the formation, such as a fracture.

Further, group identifier may be labels directly identifying the type of rocks based on formerly acquired geological data classified in a database by calculating the dissimilarity between texture indicators representative of the cluster and reference indicators relative to a type of rock in a database. Zones of interest (breakout, fractured zones) may also be identified using the above-mentioned method.

The group identifiers may be refined by the end-user if needed before validation. For example, the limits of the groups may be manually modified by the end-users. Labels may be assigned to the groups based on the geological context or when labels have already been assigned, they can be modified if necessary.

Some identifiers may be also combined by geological rules. For instance, when labels have been assigned to groups and when two adjacent segments belong to two groups that cannot correspond to adjacent layers in a geological formation according to geological models, an action may be performed. Such action may include raising an alarm or implementing a correction (such as re-assigning one of the segment to a group having neighboring texture features), optionally after checking one or several parameters relative to the borehole. Another example is to identify the repetitive pattern of segments on the image and to determine if this repetitive pattern is disturbed, in which case an alarm may be raised or a correction may be implemented.

Figure 9:
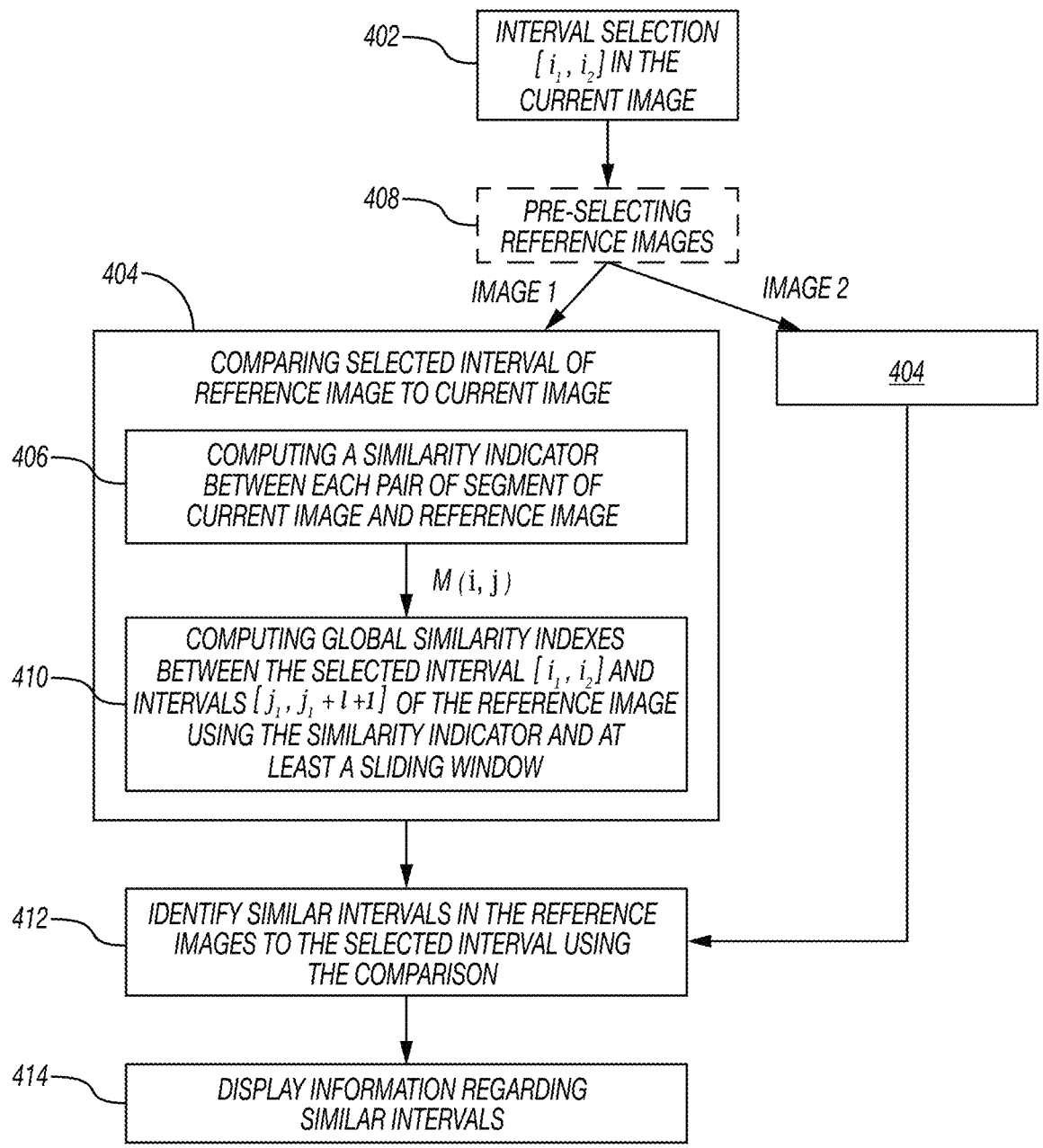
FIG. 9 is a flowchart showing details of further operations of a method according to an embodiment of the disclosure.

Furthermore, in order to help the user with the geological interpretation, the method may include retrieve one or more reference images of the database that are already interpreted and similar to the image that is under analysis as shown in a method 400 represented on FIG. 9 and performed after operation 114. This enables for instance to validate the facies determination obtained by the method disclosed in FIGS. 3A & 3B.

In order to do so, the method 400 includes selecting an interval by the user for analysis (block 402). The interval may be all or part of the segmented layers, such as an interval containing a pattern of interest.

The method then includes comparing a reference image to the image currently under analysis (block 404). The comparison includes computing a similarity indicator for each pair of segment from the image under analysis and a reference image, such as an image formerly acquired and already interpreted (block 406). The similarity indicator may be based on one or more parameter, ie the measurement that has been used to compute the image (ie resistivity or gamma-ray for instance) and/or any other log or measurement that have been taken for both the reference image and the image currently under analysis. When it is based on the measurement used to compute the image, it may be based on borehole image texture information for instance. The similarity indicator that is used for this operation may be the one that has been previously disclosed. When several parameters are taken into account, the similarity indicator may be a statistical variable (such as average, or weighted average) of the similarity indicators computed for each parameter. In other words, the similarity indicator is based on one or more parameters that are common to the image and the at least one reference image. The parameters may not be the same for different reference images, as a function of the available parameters. The operation 406 may also be computed before the interval is selected.

The output of this operation is a similarity matrix, M(i,j) (with i the identification of the segment of the image under analysis, j the identification of the segment of the reference image). Of course, several similarity matrices may be computed for comparing the image to several former reference images. The reference images may be all of the images of the database or may be pre-selected (block 408) such as filtered based on high level information. Such information may include location or type of geological environment where the reference image was logged. When there are a high number of reference images to compare to the current image, the computations may of course be parallelized in order to reduce the computation time, for instance at the referernce image level as each referernce image is independent.

Figure 10:
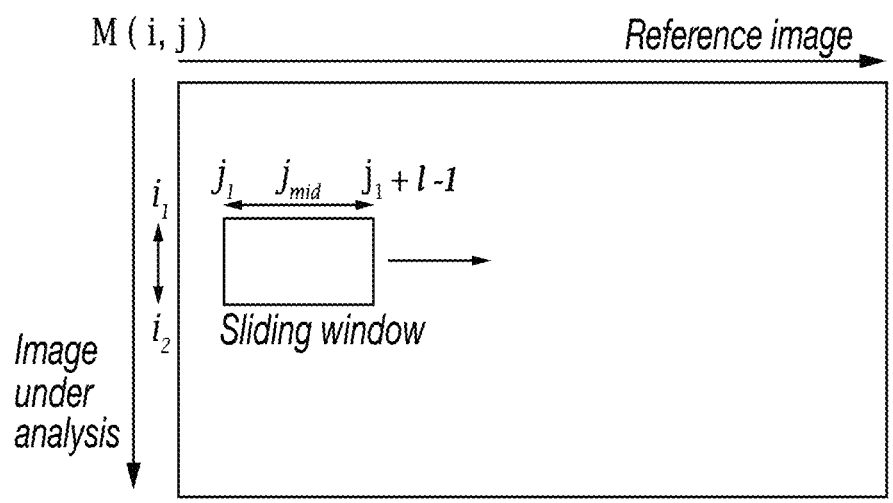
FIG. 10 is a schematic drawing showing a sliding window on a similarity matrix ad defined in the method of FIG. 9.

The method then includes computing global similarity indexes between the selected interval and intervals of the reference image, using the similarity indicator—in particular similarity matrix- and at least one sliding window (block 410), for each image. For instance, if the interval of interest in the image under analysis is the interval $[i_1, i_2]$, the global similarity index may be computed on a sliding window $[j_1, j_1+l\ 1]$ as follows, as also shown in FIG. 10:

$$globaSimilarity(j_{mid}) = \frac{2}{i_2 i_1 + 1} \sum_{i=i1}^{i=i2} \max_{j=j_1 \ldots j_1+l} M(i, j)$$

Wherein $$j_{mid} = \frac{1}{2}(j_1 + j_1 + l),$$

ie the value of the column at the middle of the interval, and wherein l is a scaling parameter.

The global similarity index is computed for every possible sliding window, ie f or $j_1$=1 . . . (# Columns l), in order to identify any similarity between intervals on the reference image and the selected interval of the image under analysis.

A reference image may be compared to the current image at a multi-scale level. Assuming that all the segments have approximately the same vertical length, when l is set to $i_2$ $i_1$+1, the reference images are compared in the similar scale as the selected interval. When l is larger, the comparison is performed on a larger scale in the reference image (i.e. stretched). One or more scaling parameters may be used for a reference image. Of course when several comparison with different scaling parameter are performed, they may be parallelized.

The global similarity index defined above is a very simple one, as it gives a high similarity if each of the segment in $[i_1, i_2]$ has at least a similar segment in the sliding window. The global similarity index may however be a different index and may for instance also take into account other constraints, such as constraints on the ordering of the layers and/or constraints on the representability of each pattern found in $[i_1, i_2]$ in the sliding window or of each pattern found in the sliding window in $[i_1, i_2]$.

The method then includes identifying similar intervals in the reference images to the selected interval in the current image using the comparison and in particular the global similarity index (block 412). The global similarity index is a function of the column; the interval where similar pattern is shown may be identified by taking the column $j_{mid}$ having high global similarity value. When several reference images are compared to image under analysis, the N columns having N maximum global index among all of the reference images and/or all of the column having global similarity index above a certain threshold may be chosen. Information regarding the similar intervals, such as the corresponding image and logs used for the analysis as well as the interpretation results (e.g. lithology classification, dip classification) and corresponding meta-data (for instance, name of the interpreter, name of the well or location, etc.) may then be displayed in the user interface (block 414). The interpreted information can be a visual guide for the interpreter and may also be used as confidence level for the user. Of course, the reference images may be pulled out of the database only if appropriate permission has been given. For instance, the reference image and associated meta-data might be displayed only if the meta-data indicate that the reference image has been taken for the same client that the one for which the current analysis is being performed.

Generally, the clustering as described in the above-mentioned method may be used as an input to numerous applications. For instance, the image segments and corresponding labels may be stored to build a dataset that may be used as a training dataset for an automatic clustering of images acquired later, coming from the same or other wells. This dataset will enable to build or refine the reference indicators for each type of rocks and to assign a label representative of the type of rock to a segment (as explained above). Once the labels relative to the type of the rocks are applied to each of the segments, they may help to identify zones of interest in the borehole, the facies of the formation intersected by the borehole. When combined to other images, they may also be used to perform a correlation analysis within a single well or a plurality of wells in the same field or to analyze a lateral variation of the facies in the field.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Generally, the disclosure related to a method for analyzing an image representative of a formation intersected by a borehole, including determining a local apparent dip of the borehole at least at a measured depth i represented on the image, applying at least a window to the image, wherein each of the windows includes one of the measured depth i and is shaped as a function of the determined local dip at the corresponding measured depth i, comparing a texture of at least a first zone of each window and a texture of at least a second zone of said window, wherein each of the first and second zones are adjacent and shaped as a function of the determined dip, determining a location of at least a texture boundary on the image based on the comparison, and deriving from the location of the at least one texture boundary at least a property of the formation.

Each of the windows and of the first and second zones may be delineated in at least a direction of the image so as to follow the apparent dip.

Applying at least a window to the image may include applying a sliding window to the image.

Further, comparing the texture of a first and second zones of the window may include performing a unique comparison per window. The first and second zones may in particular have a predetermined shape identical for each of the windows.

Alternatively, a plurality of first and second zones having a corresponding intersection may be compared per window The window may be shaped so that its dimension perpendicular to the dip is not greater than twice a minimal thickness of a layer.

The comparison may also include calculating a likelihood of a texture boundary at the intersection between the first and second zones based on the comparison. The likelihood calculation may for instance based on a STSIM (Structural Texture Similarity) indicator or on a distance between vectors characterizing each zone and computed using filters such as Gabor filters.

The method may include plotting a curve representative of the likelihood of a texture boundary at the intersection versus the location of the intersection.

Determining the location of the texture boundary according to the method may include determining the locations associated with a likelihood value that satisfies at least one predetermined condition. The at least one condition includes at least one of the below conditions:

the likelihood value of the location is in a predetermined range, the likelihood value of the location is a local maximum of the likelihood values set, the likelihood value of the location is part of a set of likelihood values that maximizes a sum of likelihood value while their corresponding locations are distant of at least a predetermined distance, corresponding in particular to the minimal width of a layer.

In an embodiment of the method, the formation property includes a location of at least a bed boundary.

In another embodiment, the formation property includes a facies of the formation intersected by the borehole. Both properties may however be determined after the texture boundaries have been determined. Determining the facies may comprise segmenting the image in several segments based on the determined texture boundary, wherein a plurality of segments are each delineated by adjacent texture boundaries. Determining the facies may also comprise clustering segments into groups based on texture features representative of each segment, wherein two different segments may be assigned to an identical group. Each cluster may also be assigned to a type of rock, by comparison of at least an indicator representative of the cluster with the at least one indicator representative of the type of rock in a database (including for instance reference type of rocks extracted from previously analyzed formations).

The method may also include comparing a predetermined interval of the image to at least a reference image, identifying in the reference image at least one interval similar to the predetermined interval and displaying information regarding the similar interval. In this embodiment, comparing may include computing a similarity indicator between each pair of segment of the image and of the at least one reference image and, based on the similarity indicator, computing a global similarity index between the predetermined interval and at least an interval of the at least one reference image. The similarity indicator is based on one or more parameters that are common to the image and the at least one reference image. The parameters may not be the same for different reference images, as a function of the available parameters. The global similarity index may be computed taking into account interval of different scales.

The method may also include measuring at least a downhole parameter of the borehole in order to obtain the borehole image.

The image may be a downhole acoustic image, a downhole electromagnetic image, a downhole gamma-ray spectral image of a borehole wall, a photograph of the borehole wall or of a rock core of the formation, or a CT scan of a rock core of the formation.

The disclosure also relates to a method for analyzing an image representative of a geological formation intersected by a borehole, including determining a location of at least a texture boundary on the image, segmenting the image in several segments based on the determined texture boundary, wherein a plurality of segments are each delineated by adjacent texture boundaries, clustering segments into groups based on texture features representative of each segment, wherein two different segments may be assigned to an identical group, and determining a facies of a formation based on the clustering.

The image may be a downhole acoustic image, a downhole electromagnetic image, a downhole gamma-ray spectral image of a borehole wall, a photograph of the borehole wall or of a rock core of the formation, or a CT scan of a rock core of the formation.

In an embodiment of the method, each cluster may be assigned to a type of rock, by comparison of at least an indicator representative of the cluster with the at least one indicator representative of the type of rock in a database (including for instance reference type of rocks extracted from previously analyzed formations).

The method may also include comparing a predetermined interval of the image to at least a reference image, identifying in the reference image at least one interval similar to the predetermined interval and displaying information regarding the similar interval. In this embodiment, comparing may include computing a similarity indicator between each pair of segment of the image and of the at least one reference image and, based on the similarity indicator, computing a global similarity index between the predetermined interval and at least an interval of the at least one reference image. The similarity indicator is based on one or more parameters that are common to the image and the at least one reference image. The parameters may not be the same for different reference images, as a function of the available parameters. The global similarity index may be computed taking into account interval of different scales.

The second method according to the disclosure and disclosed may include all or part of the first method according to the disclosure.

The method may also include determining a local apparent dip of the borehole at least at a measured depth i represented on the image, applying at least a window to the image, wherein each of the windows includes one of the measured depth i and is shaped as a function of the determined local dip at the corresponding measured depth i, comparing a texture of at least a first zone of each window and a texture of at least a second zone of said window, wherein each of the first and second zones are adjacent and shaped as a function of the determined dip, wherein the at least one texture boundary is determined based on the comparison.

The disclosure also relates to a system for analyzing an image representative of a formation intersected by a borehole, wherein the system includes a set of processors comprising at least a processor and configured for determining a local apparent dip of the borehole at least at a measured depth i represented on the image, applying at least a window to the image, wherein each of the windows includes one of the measured depth i and is shaped as a function of the determined local dip at the corresponding measured depth i, comparing a texture of at least a first zone of each window and a texture of at least a second zone of said window, wherein each of the first and second zones are adjacent and shaped as a function of the determined dip, determining a location of at least a texture boundary on the image based on the comparison, and deriving from the location of the at least one texture boundary at least a property of the formation.

The system of claim may also include a downhole tool for measuring at least a property of the borehole and obtain a borehole image.

Generally the system and especially the set of processors may be configured to perform all of the operations disclosed in relationship with the methods above.

The disclosure also relates to a system for analyzing an image representative of a geological formation, wherein the system includes a set of processors comprising at least a processor and configured for determining a location of at least a texture boundary on the image, segmenting the image in several segments based on the determined texture boundary, wherein a plurality of segments are each delineated by adjacent texture boundaries, clustering segments into groups based on texture features representative of each segment, wherein two different segments may be assigned to an identical group, and determining a facies of a formation based on the clustering.

The system may also include a downhole tool for measuring at least a property of the borehole and obtain a borehole image.

Generally the system and especially the set of processors may be configured to perform all of the operations disclosed in relationship with the methods above.

The disclosure also related to a machine readable storage medium having stored thereon a computer program for analyzing an image representative of a geological formation, the computer program comprising a routine of set instructions for causing the machine to determine a local apparent dip of the borehole at least at a measured depth i represented on the image, apply at least a window to the image, wherein each of the windows includes one of the measured depth i and is shaped as a function of the determined local dip at the corresponding measured depth i, compare a texture of at least a first zone of each window and a texture of at least a second zone of said window, wherein each of the first and second zones are adjacent and shaped as a function of the determined dip, determine a location of at least a texture boundary on the image based on the comparison, and derive from the location of the at least one texture boundary at least a property of the formation.

It also related to a machine readable storage medium having stored thereon a computer program for analyzing an image representative of a geological formation, the computer program comprising a routine of set instructions for causing the machine to determine a location of at least a texture boundary on the image, segment the image in several segments based on the determined texture boundary, wherein a plurality of segments are each delineated by adjacent texture boundaries, cluster segments into groups based on texture features representative of each segment, wherein two different segments may be assigned to an identical group and determine a facies of a formation based on the clustering.

The invention claimed is:

1. A method for analyzing an image representative of a formation intersected by a borehole, including:
   determining a local apparent dip of the borehole at least at a measured depth i represented on the image,
   applying at least one window to the image, wherein each of the at least one window includes one of the measured depth i and is shaped as a function of the determined local dip at the corresponding measured depth i,
   comparing a texture of at least a first zone of each window and a texture of at least a second zone of said window, wherein each of the first and second zones are adjacent and shaped as a function of the determined dip,
   determining a location of at least a texture boundary on the image based on the comparison,
   deriving from the location of the at least one texture boundary at least a property of the formation.

2. The method of claim 1, wherein each of the windows and of the first and second zone are delineated in at least a direction of the image so as to follow the apparent dip.

3. The method of claim 1, wherein applying at least a window to the image includes applying a sliding window to the image.

4. The method of claim 3, wherein comparing the texture of a first and second zone of the window includes performing a unique comparison per window, wherein the first and second zones have a predetermined shape identical for each of the windows.

5. The method of claim 1, wherein the window is shaped so that its dimension perpendicular to the dip is not greater than twice a minimal thickness of a layer.

6. The method of claim 1, including calculating a likelihood of a texture boundary at the intersection between the first and second zones based on the comparison.

7. The method of claim 6, wherein determining the location of the texture boundary includes determining the locations associated with a likelihood value that satisfies at least one predetermined condition.

8. The method of claim 7, wherein the at least one condition includes at least one of the below conditions:
   the likelihood value of the location is in a predetermined range,
   the likelihood value of the location is a local maximum of the likelihood values set,
   the likelihood value of the location is part of a set of likelihood values that maximizes a sum of likelihood value while their corresponding locations are distant of at least a predetermined distance, corresponding in particular to the minimal width of a layer.

9. The method according to claim 1, wherein the formation property includes a location of at least a bed boundary and/or a facies of the formation intersected by the borehole.

10. The method according to claim 1, wherein the formation property includes a facies of the formation intersected by the borehole and wherein determining the facies comprises segmenting the image in several segments based on the determined texture boundary, wherein a plurality of segments are each delineated by adjacent texture boundaries.

11. The method according to claim 10, wherein determining the facies comprises clustering segments into groups based on texture features representative of each segment, wherein two different segments may be assigned to an identical group.

12. The method according to claim 1, wherein the image is a downhole acoustic image, a downhole electromagnetic image, a downhole gamma-ray spectral image of a borehole wall, a photograph of the borehole wall or of a rock core of the formation, or a CT scan of a rock core of the formation.

13. A method for analyzing an image representative of a geological formation intersected by a borehole, wherein the image is based on measurements taken by a downhole tool lowered in the borehole, including:
- determining a location of at least a texture boundary on the image,
- segmenting the image in several segments based on the determined texture boundary, wherein a plurality of segments are each delineated by adjacent texture boundaries,
- clustering segments into groups based on texture features representative of each segment, wherein two different segments may be assigned to an identical group
- determining a facies of a formation based on the clustering.

14. The method according to claim 13, wherein each cluster may be assigned to a type of rock, by comparison of at least an indicator representative of the cluster with the at least one indicator representative of the type of rock in a database.

15. The method according to claim 13, including:
- determining a local apparent dip of the borehole at least at a measured depth i represented on the image,
- applying at least one window to the image, wherein each of the at least one window includes one of the measured depth i and is shaped as a function of the determined local dip at the corresponding measured depth i,
- comparing a texture of at least a first zone of each window and a texture of at least a second zone of said window, wherein each of the first and second zones are adjacent and shaped as a function of the determined dip,
- wherein the at least one texture boundary is determined based on the comparison.

16. The method according to claim 13, including comparing a predetermined interval of the image to at least a reference image, identifying in the reference image at least one interval similar to the predetermined interval and displaying information regarding the similar interval of the reference image.

17. The method according to claim 16, wherein comparing includes computing a similarity indicator between each pair of segment of the image and of the at least one reference image and, based on the similarity indicator, computing a global similarity index between the predetermined interval and at least an interval of the at least one reference image.

18. A system for analyzing an image representative of a geological formation intersected by a borehole, wherein the image is based on measurements taken by a downhole tool lowered in the borehole, wherein the system includes a set of processors comprising at least a processor and configured for:
- determining a location of at least a texture boundary on the image,
- segmenting the image in several segments based on the determined texture boundary, wherein a plurality of segments are each delineated by adjacent texture boundaries,
- clustering segments into groups based on texture features representative of each segment, wherein two different segments may be assigned to an identical group
- determining a facies of a formation based on the clustering.

19. The system of claim 18, including a downhole tool for measuring at least a property of the borehole and obtain a borehole image.

20. The system of claim 18, wherein the set of processors is configured for:
- determining a local apparent dip of the borehole at least at a measured depth i represented on the image,
- applying at least one window to the image, wherein each of the at least one window includes one of the measured depth i and is shaped as a function of the determined local dip at the corresponding measured depth i,
- comparing a texture of at least a first zone of each window and a texture of at least a second zone of said window, wherein each of the first and second zones are adjacent and shaped as a function of the determined dip, and
- determining a location of at least a texture boundary on the image based on the comparison.

* * * * *